(12) United States Patent
Ferrari (10) Patent No.: US 8,409,128 B2
(45) Date of Patent: Apr. 2, 2013

(54) DEVICE FOR SUPPORTING THE HEART AND CIRCULATORY SYSTEM

(75) Inventor: Markus Ferrari, Jena (DE)

(73) Assignee: MWF Consult Ltd., Jena (DE)

( * ) Notice: Subject to any disclaimer, the term of this patent is extended or adjusted under 35 U.S.C. 154(b) by 753 days.

(21) Appl. No.: 12/531,129

(22) PCT Filed: Mar. 17, 2008

(86) PCT No.: PCT/EP2008/053164
§ 371 (c)(1),
(2), (4) Date: Dec. 7, 2009

(87) PCT Pub. No.: WO2008/113785
PCT Pub. Date: Sep. 25, 2008

(65) Prior Publication Data
US 2010/0087773 A1    Apr. 8, 2010

(30) Foreign Application Priority Data
Mar. 16, 2007    (DE) .......................... 10 2007 012 817

(51) Int. Cl.
*A61M 5/00*    (2006.01)
(52) U.S. Cl. ............................................... 604/9; 604/7
(58) Field of Classification Search .................. 604/4.01, 604/5.01, 6.01, 6.09–6.11, 8–107; 606/16–18; 623/3.1, 3.11, 3.16–3.17
See application file for complete search history.

(56) References Cited

U.S. PATENT DOCUMENTS 4,245,622 A    1/1981    Hutchins, IV ................... 128/1

(Continued)

FOREIGN PATENT DOCUMENTS

| WO | WO 00/03754 | 1/2000 |
|---|---|---|
| WO | WO 2004/078234 | 9/2004 |

OTHER PUBLICATIONS

"Notification of Transmittal of Translation of the International Preliminary Report on Patentability . . . " for PCT/EP2008/053164 dated Oct. 15, 2009; 9 pages.
Official Action from German Application No. 102007012817.9-55, dated Nov. 21, 2007.

(Continued)

*Primary Examiner* — Philip R Wiest
(74) *Attorney, Agent, or Firm* — Westman, Champlin & Kelly, P.A.

(57) ABSTRACT

The present invention relates to a device for circulating a body fluid in a body of a living organism, especially to support the heart and/or circulation of the living organism, comprising a catheter device which has at least one inlet portion to take up the body fluid at at least one first location within the body of the living organism, at least one outlet portion some distance from the at least one inlet portion to discharge the body fluid at at least one second location some distance from the at least one first location within the body of the living organism and a pump device for directed transport of the body fluid between the at least one inlet portion and the at least one outlet portion of the catheter device; and a valve arrangement coupled to the catheter device for controlled uptake of the body fluid as a function of operation of the pump device at the at least one inlet portion of the catheter device and controlled discharge of the body fluid at the at least one outlet portion of the catheter device.

7 Claims, 5 Drawing Sheets

U.S. PATENT DOCUMENTS

| | | | | |
|---|---|---|---|---|
| 4,906,229 | A | | 3/1990 | Wampler ........................ 600/16 |
| 5,169,378 | A | * | 12/1992 | Figuera .......................... 600/16 |
| 5,928,132 | A | * | 7/1999 | Leschinsky .................... 600/16 |
| 6,395,026 | B1 | | 5/2002 | Aboul-Hosn et al. ....... 623/3.13 |
| 6,607,368 | B1 | | 8/2003 | Ross et al. .................... 417/412 |

OTHER PUBLICATIONS

International Search Report for PCT/EP2008/053164; dated Nov. 11, 2008.

* cited by examiner

DEVICE FOR SUPPORTING THE HEART AND CIRCULATORY SYSTEM

CROSS REFERENCE TO RELATED APPLICATIONS

This application is a Section 371 National Stage Application of International Application No. PCT/EP2008/053164, filed Mar. 17, 2008, published in German, which claims the benefit of German patent application No. 10 2007 012 817.9, filed Mar. 16, 2007, the entire disclosure of which is herein incorporated by reference.

FIELD OF THE INVENTION

The present invention relates to a device for supporting the heart and circulatory system.

Patients with acute cardiac insufficiency suffer from underperfusion of vital organs. The reduced supply of oxygen-rich blood in the circulatory system also leads to increased cardiac insufficiency, as the heart itself is also underperfused. It is thus necessary to support the heart and the circulation in the case of acute cardiac insufficiency.

The use of certain drugs to increase cardiac action is known in the art. Since drugs can certainly increase cardiac action in the short term, although at the expense of cardiac metabolism, circulation must be maintained with the aid of external energy supplies in the case of acute heart failure or acute cardiac insufficiency.

Mechanical circulation support systems have proved themselves in this field by either supporting cardiac action (intra-aortic balloon counterpulsation, IABP for short) or increasing the circulation volume by inherent pump action (axial screw pumps, extracorporeal circulation systems with centrifugal pump). The use of such systems is limited by their cost, on the one hand, and by the options for fitting such systems such that they are minimally invasive on the other hand. As these pump systems are generally connected to the patient's circulatory system via the inguinal vessels, this leads to limited capacity due to the inner diameter of the vessel.

Intra-aortic balloon counterpulsation (IABP) is one system which is known to the applicant. In this system, a balloon tube filled with helium gas is taken from the femoral artery to the descending thoracic aorta with a catheter and inflated or evacuated abruptly at this point in the opposite direction to the heart. The action of IABP causes the afterload for the left chamber of the heart to fall, resulting in a reduction in myocardial oxygen consumption. Inflating the balloon abruptly in the diastole phase causes the blood pressure to rise and thus leads to improved perfusion of the heart and organs.

The disadvantage of this approach has been shown to be the fact that IABP only causes a sufficient increase if the heart's own capacity is adequate. IABP is ineffective in functional terms in the event of cardiac arrest. An IABP unit is contraindicated in patients who display a higher level of aortic valve incompetence, as the left ventricle can be overloaded as a result of inflating the IABP balloon.

SUMMARY OF THE INVENTION

The object of the present invention is to create a device which supports the heart and the circulation and which eliminates the disadvantages described above.

According to the invention, a device is proposed for circulating a body fluid in a body of a living organism, especially to support the heart and/or circulation of the living organism, which has a catheter device which has at least one inlet portion to take up the body fluid at at least one first location within the body of the living organism, at least one outlet portion some distance from the at least one inlet portion to discharge the body fluid at at least one second location some distance from the at least one first location within the body of the living organism and a pump device for directed transport of the body fluid between the at least one inlet portion and the at least one outlet portion of the catheter device; and a valve arrangement coupled to the catheter device for controlled uptake of the body fluid as a function of operation of the pump device at the at least one inlet portion of the catheter device and controlled discharge of the body fluid at the at least one outlet portion of the catheter device.

Compared with the specified prior art, the present invention therefore has the advantage of guaranteeing a large pump capacity with minimal external surface and a small diameter on the heart. It is also possible to provide cardiac support and stabilise the circulation gradually or synchronised with cardiac action. As blood can be actively sucked out of the left ventricle, for example, by means of the pump device, the device can also be used on patients who have a higher level of aortic valve incompetence.

By modifying the device slightly, it can be used advantageously either in the left heart chamber or in the right heart chamber as required.

The sub-claims provide further details of advantageous embodiments of the device according to the invention.

Embodiments of the invention are explained below in greater detail with the aid of the drawing figures.

DETAILED DESCRIPTION OF THE DRAWINGS

In the figures, the same reference numerals refer to the same components or components with the same function, unless otherwise specified.

At this point it should be noted that liquid movements and/or flow directions are shown in the figures by means of arrows.

Figure 1A:
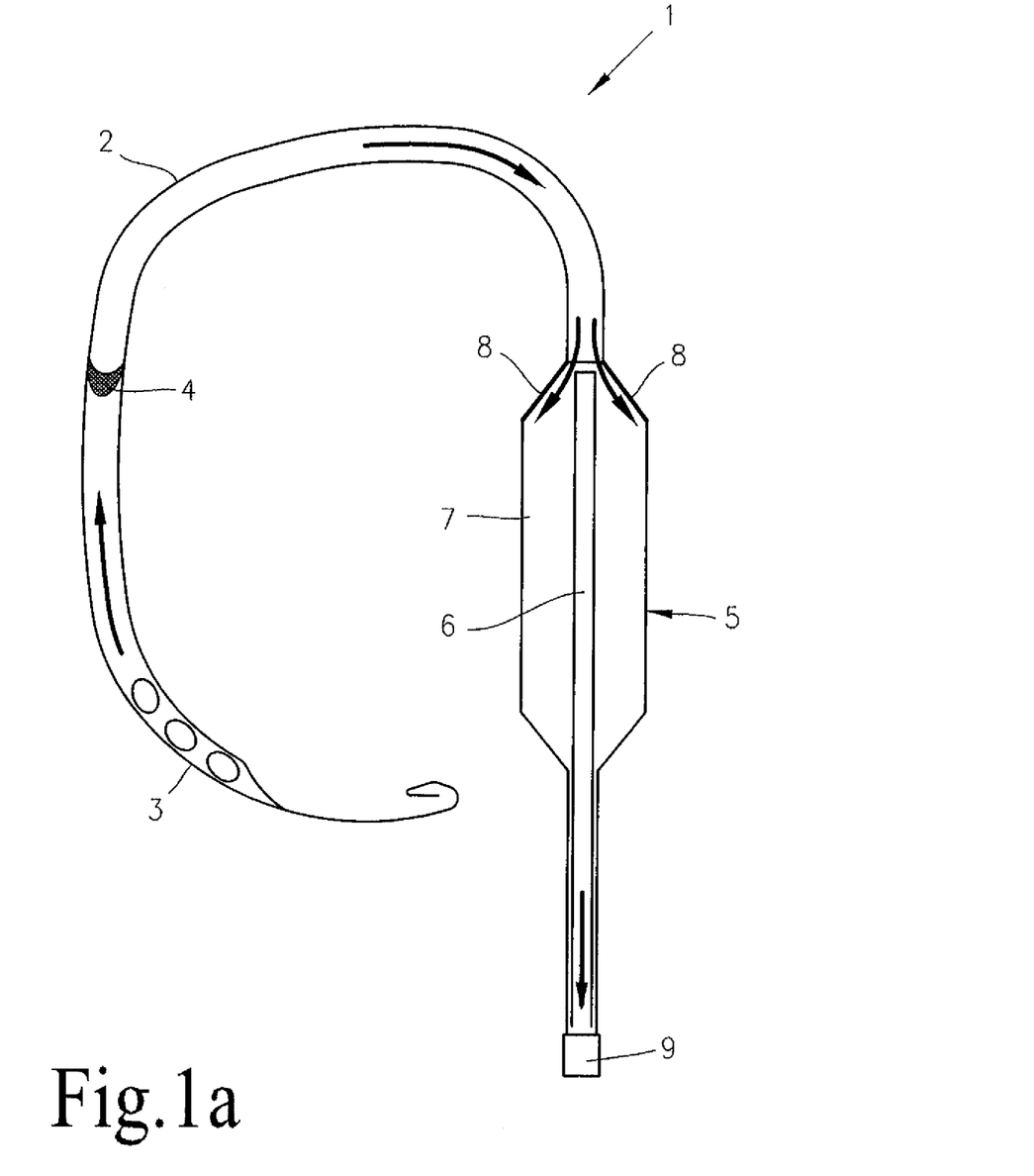
FIG. 1a a schematic representation of a device to support the heart/circulation in accordance with a preferred embodiment of the present invention in a first state.
Figure 1B:
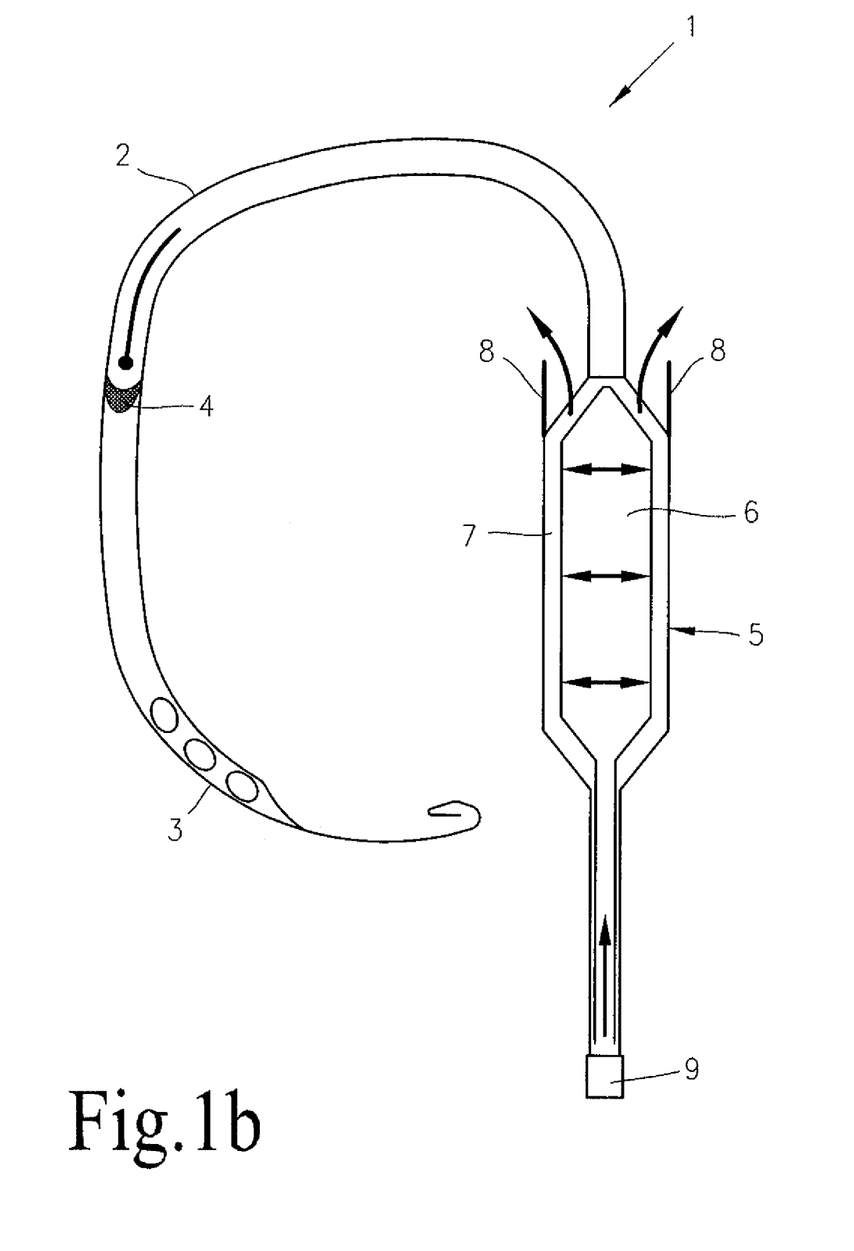
FIG. 1b a schematic representation of the device in FIG. 1a in a second state.

FIGS. 1a and 1b each show a device 1 to support the heart and/or circulation of a living organism according to a preferred embodiment of the present invention. Of these, FIG. 1a shows the device 1 in a first state and FIG. 1b shows the device 1 in a second state.

As shown in FIGS. 1a and 1b, the device 1 has a pump cannula 2 which is used to transport the body fluids from a first location to a second location inside the body of the living organism. A cannula end 3 with opening areas is located at one end of the pump cannula 2. In the present embodiment, the cannula end 3 is, for example, used as an inlet portion to take up the body fluid from the first location inside the body of the living organism. The cannula end 3 may also be referred to as the suction cannula 3 according to the present embodiment. FIGS. 1*a* and 1*b* also show that an inlet valve 4 is located adjacent to the cannula end 3 inside the pump cannula 2 and in the open state as per FIG. 1*a* this valve allows the body fluid to flow through from the cannula end 3 and in the closed state, as per FIG. 1*b*, it no longer allows the body fluid to flow back to the cannula end 3.

In the region of the opposite end of the device 1 to the cannula end 3, there is an integral pump device 5 which may, for example, consist of a collapsible double chamber cavity with an internal chamber 6 and an outer chamber 7. In addition, the pump device 5 consists of several, for example two outlet valves 8. The outlet valves 8 are, for example, an integral part of an outlet portion of the device in the outer wall of the outer chamber 7 of the pump device 5, this outlet portion being provided adjacent to the pump cannula 2. However, it is obvious to an expert that the location, number and configuration of the inlet and outlet valves can be designed, modified and optimised in accordance with the usage in question.

A drive mechanism 9 is also preferably coupled to the pump device 5 and this drive mechanism is shown schematically in FIGS. 1*a* and 1*b* by means of reference numeral 9. The drive mechanism may for example take the form of an external drive mechanism or a miniature integral drive mechanism within the body of the living organism or may be designed in some other advantageous fashion.

Figure 2:
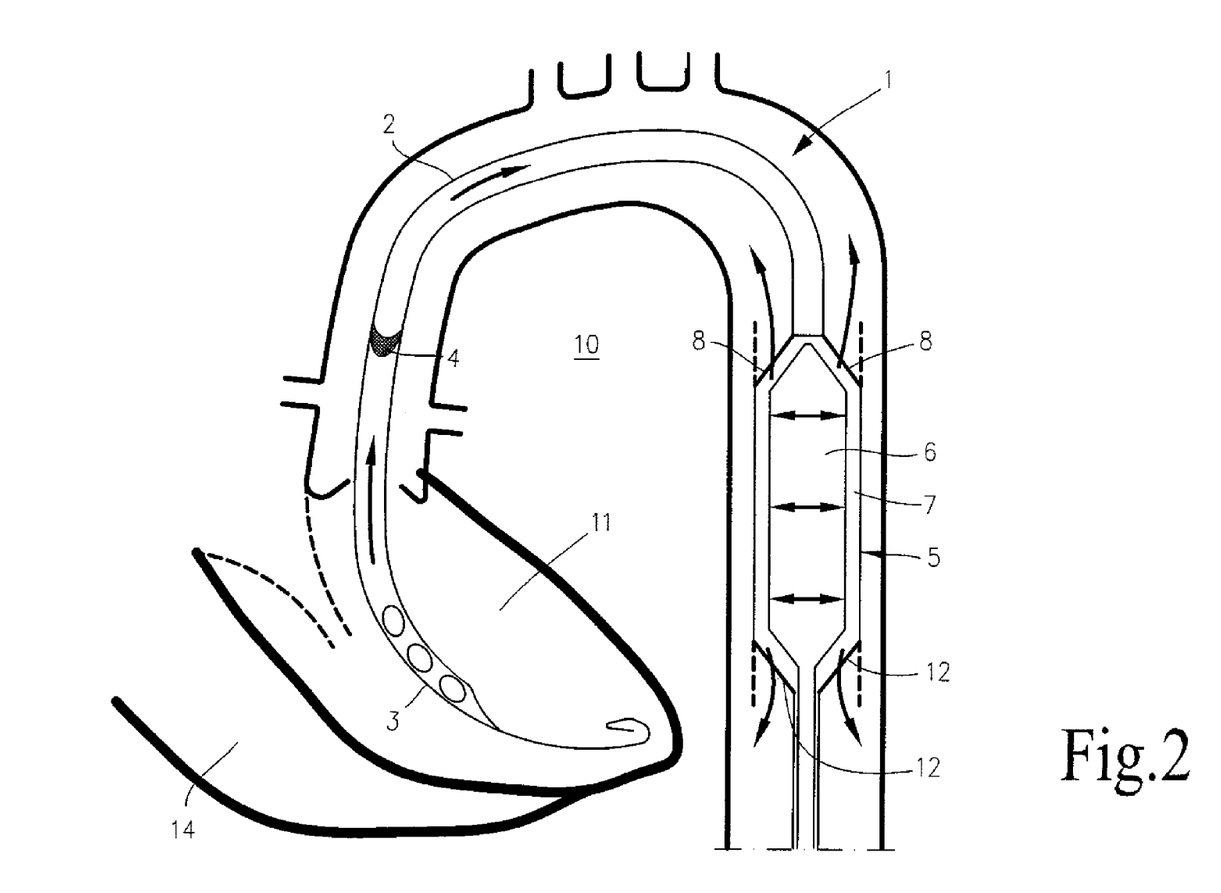
FIG. 2 a schematic representation of a device to support the heart/circulation in accordance with a further preferred embodiment of the present invention, the device being arranged and used to support the left chamber of the heart.

FIG. 2 shows a schematic representation of a device 1 in accordance with a further preferred embodiment. In FIG. 2 the device 1 is, for example, fitted in the left ventricle or in the left chamber of the heart 11 to support the heart. When the inlet valve 4 is opened, blood is sucked from the left ventricle 11 into the outer chamber 7 of the pump device 5 via the pump cannula 2, as illustrated schematically in FIG. 1*a*. On inflating the inner chamber 6 of the pump device 5, in the form of a pump balloon for example, the blood is then discharged into the circulatory system by means of the outlet valves 8 (see schematic representation in FIG. 1*b*, FIG. 2 and FIG. 3).

The cannula end 3 may, for example, be straight or may have a pigtail end. The entire catheter is, for example, inserted in the aortic arch via the inguinal vessels, the pump device being located in the descending aorta.

Unlike the device according to the first embodiment as shown in FIGS. 1*a* and 1*b*, the device 1 according to the present embodiment as shown in FIG. 2 has two lower outlet valves 12 in the outer wall of the outer pump chamber 7 in addition to the two upper outlet valves 8.

The mode of operation of the device 1 is described below in greater detail.

Figure 3:
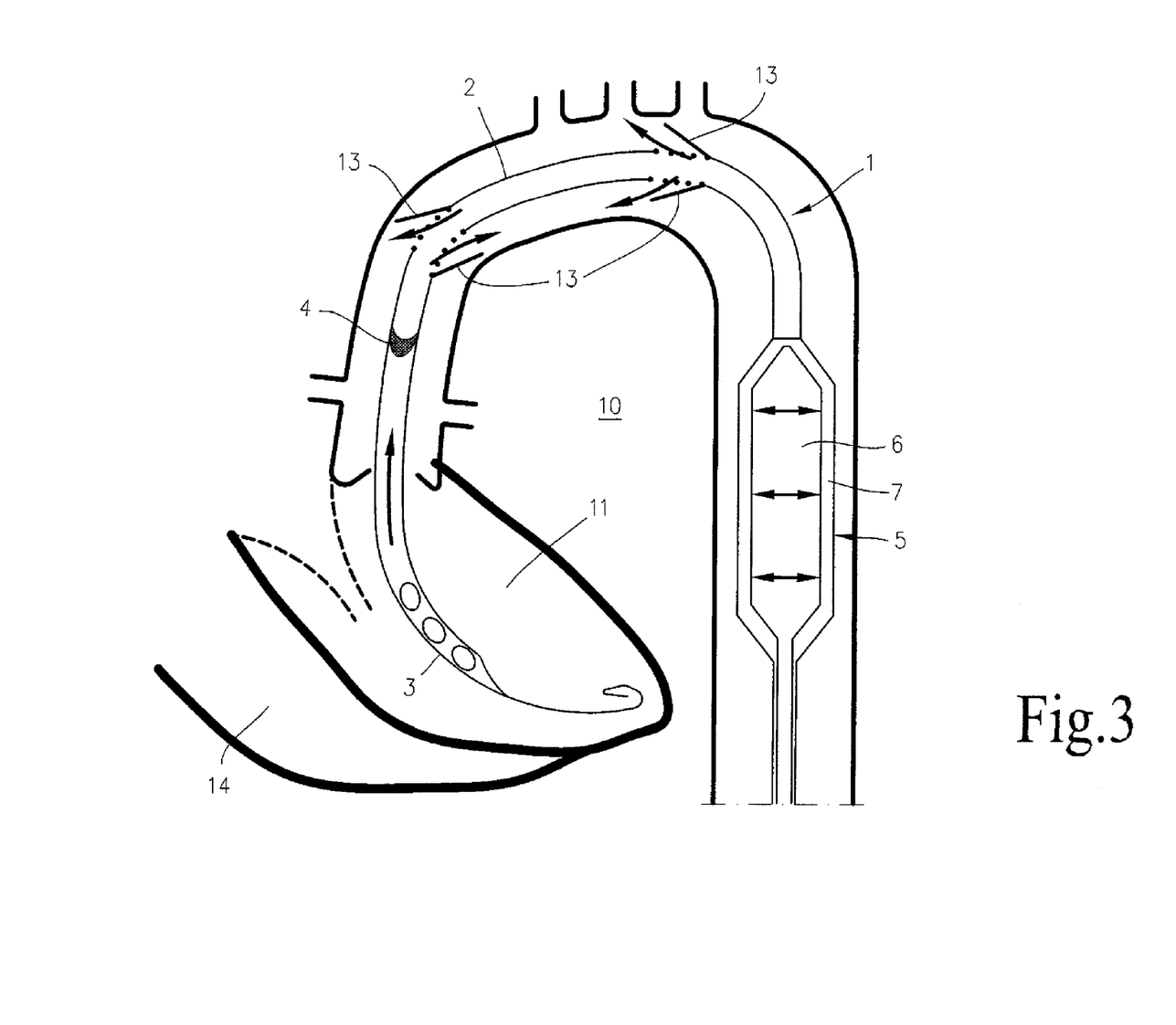
FIG. 3 a schematic representation of a device to support the heart/circulation in accordance with a further preferred embodiment of the present invention, the device being arranged and used to support the left chamber of the heart.

FIG. 3 shows a device 1 according to a further preferred embodiment of the invention, which is also designed and fitted in such a way as to support the left chamber of the heart 11. Unlike the embodiment shown in FIG. 2, the device 1 does not have any outlet valves in the region of the pump device 5. Outlet valves 13 are provided in the region of the wall for the pump cannulas 2 between the pump device 5 and the inlet valve 4. However, it is evident to an expert that the number and configuration of the outlet valves 12 can be varied accordingly and that a combination of the embodiments shown in FIGS. 2 and 3 is also conceivable.

The device according to the invention to support the heart and circulation as shown in FIGS. 1 to 3 consists of a suction cannula 3 which lies in the left chamber of the heart 11, which guarantees an optimum flow of blood into the pump cannula 2 thanks to corresponding refinements. A directed flow of blood through the pump cannula 2 is ensured by an inlet valve 4. The driving pump device 5 at the end of the pump cannula 2 consists of a collapsible double chamber cavity which leads to a volume displacement inside the pump system through at least one fluid-filled pump chamber 6. The blood is pressed out via outlet valves 8, 12, 13 on the pump cannula 2 or on the pump device 5 whilst the pump chamber 6 is inflated with fluid. The outlet valves 8, 12, 13 ensure that the body fluid flows out in a directed manner and prevent it flowing back in again in the filling phase. Thus, a directed flow can be ensured within the body, causing an improvement in the circulating volume and accordingly in organ perfusion as well as providing cardiac support.

As the described pump catheter 1 sucks blood out of the left ventricle (=active support), it can also be used on patients who have a higher level of aortic valve incompetence (which is actually a contraindication for the use of IABP).

Figure 4:
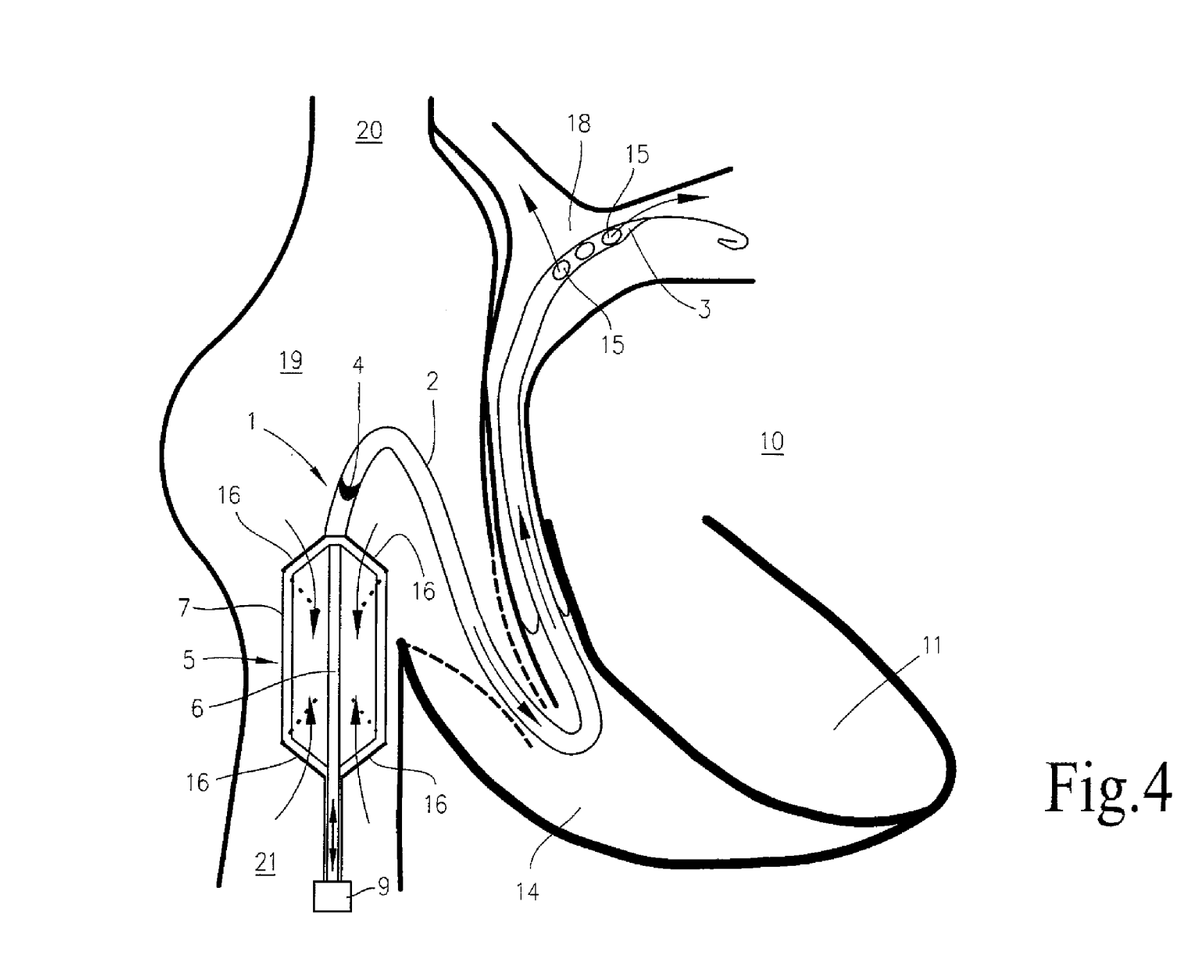
FIG. 4 a schematic representation of a device to support the heart/circulation in accordance with a further preferred embodiment of the present invention, the device being arranged and used to support the right chamber of the heart.

FIG. 4 shows a device 1 to support the right chamber of the heart 14. The device 1 according to the embodiment shown in FIG. 4 is designed such that the pump device 5 has several inlet valves 16 which are arranged in the region of the outer wall of the outer chamber 7 of the pump device 5 similarly to the outlet valves 8 in the embodiment shown in FIG. 2. The inlet valve 4 is also located inside the pump cannula 2 adjacent to the pump device 5. The opposite end to the pump device, i.e. the cannula end 3 of the device 1 preferably has several outlet valves or outlet apertures 15, which means that the body fluid can be transported from the pump device 5 via the pump cannula 2 to the cannula end 3 and can be discharged to the living organism's circulatory system via the outlet valves or apertures 15 at this point.

FIG. 4 thus shows en embodiment of a version of the device for supporting the right chamber of the heart 14. As a result, a portion of the device can also be fitted in the pulmonary artery 18, to support the right ventricle 14. In this case the inlet portion of the device 1 is in the right atrium 19, the right ventricle 14 or the vena cava, especially as a jugular insert in the vena cava superior 20 and as a femoral implant in the vena cava inferior 21.

The pump device 5 can also be used in the right chamber of the heart 14, as shown in FIG. 4 by modifying the device as shown in FIGS. 1 to 3. In this case the suction cannula or the cannula end 3 ends in the region of the pulmonary artery. The valves 16 in the region of the pump device 5 at the level of the right atrium or in the region of the caval vein ensure that blood flows in at the point when the inner pump chamber 6 does not contain any fluid. When filling the inner pump chamber 6 with fluid, the inlet valves on the outer pump chamber 7 close and the blood is transported onwards into the pulmonary artery through the pump catheter 2 up to the outlet tip. Such an application of a right ventricular support system based on the device according to the invention can be used to support patients with acute right ventricular failure. These patients often suffer organ damage as a result of blood blockages, which can be resolved with this system due to improved transport away from the right atrium and the vena cava.

The present invention combines the advantages of the intra-aortic balloon pump to reduce afterload and improved organ perfusion with the concept of axial screw pumps, which could previously only be operated with microturbines.

A device 1 is described to support the heart and the circulatory system for circulation of body fluids, the liquid-holding cavity in the device 1 having at least one pipe or pump cannula 2 through which the body fluid can flow with at least one inlet and at least one outlet. According to the invention the pump catheter 2 and the pump chamber 5 are equipped with valves with the aim of transporting body fluids in a directed fashion within the body. In the pump chamber the body fluid is sucked in or pressed out through a pump chamber 5 which is intermittently filled with fluid by means of an external drive 9. The pressure amplitude, pump speed and the time ratio between filling and emptying can be varied during this process and adapted to requirements. This can be triggered during the process as a function of pressures in the cavities, electrical pulses or flow signals. However, an independent (internal) pump action is also possible with frequency, amplitude and phase selected at will. The system can be fitted percutaneously by radioscopy, ultrasound or even by guiding catheter and/or guide wire without imaging after puncturing the vessel.

The described circulation support system can be fitted through the skin. Position control when fitting the system is possible percutaneously by means of radioscopy, ultrasound or even by means of guiding catheter and/or guide wire without imaging (e.g. during resuscitation) after puncturing the vessel. Measuring the pressure at the catheter tip may provide information with regard to the correct position of the pump catheter 1. The external pump chamber 7 can be set up and fitted in a mechanically stable state by external manipulation by design-dependent stabilisation of the outer pump chamber 7 with a plurality of collapsible webs or corresponding shaping of the outer covering. In this case the size and the structure of this outer pump chamber 7 are designed such that they do not lead to a complete misplacement of the large vessel (aorta, vena cava). The inner part 6 of the pump chamber can either be fitted at the same time as the outer part 7 of the pump chamber or may be introduced at a later date by an internal lumen provided accordingly. In order to remove the catheter system or the device 1, the internal chamber 6 is evacuated and, if applicable, removed again in the correspondingly reversed sequence. The outer pump chamber 7 is collapsed again and can be pulled outwards via the percutaneous access route.

The advantages of the described solution according to the invention are due to the minimally invasive insertion and removal of the system thanks to its collapsibility, the simplicity of the pump drive without any rotating foreign bodies which may lead to an increased destruction of blood cells (haemolysis), the combination of cardiac support and simultaneous circulatory support, and the simplicity of a universally exchangeable drive mechanism. Such drive consoles as are designed for intra-aortic balloon pumps (IABP) are available in many clinics. These drive consoles can also be used to operate the present invention, which is why additional technical apparatus do not need to be provided separately in this case. As a result, this system not only represents a useful medical addition to circulatory support systems which are currently available, but also a useful economic addition. The opportunity to use the device in the left and right chambers of the heart and whilst using two external drives, also on both chambers of the heart simultaneously, represents a further medical improvement in treating patients with acute cardiac insufficiency.

The present invention thus provides a device for supporting the heart and the circulatory system for the circulation of body fluids, the liquid-holding cavity having at least one pipe through which the body fluid can flow with at least one inlet and at least one outlet, transfer of the body fluids taking place in a directed fashion within the body. The pump catheter and the pump chamber are provided with valves in this case. In the pump chamber the body fluid is sucked in or pressed out through a pump chamber which is intermittently filled with fluid by means of a pneumatic drive which is located externally or implanted in the body in a miniature version. The pressure amplitude, pump speed and the time ratio between filling and emptying can be varied at will during this process and adapted to requirements. This can be triggered as a function of pressures in the cavities, electrical pulses or flow signals or an independent (internal) pump action with frequency, amplitude and phase which can be selected at will. The pump catheter can also have a collapsible and thus expandable pump chamber which can be collapsed again for removal. The pump catheter can also be fitted and fed in without surgical measures, i.e. merely by puncturing the skin via a peripheral vein (right heart) or artery (left heart). The pump catheter can advantageously be fitted and removed again subsequently under local anaesthetic and also during resuscitation and circulatory failure. Operation of the pump catheter with a commercially available drive unit for an intra-aortic balloon pump (IABP) can be arranged. The pump process can be used to support the right or left chamber of the heart or for both chambers of the heart (2-pump catheter) according to the version. The described pump catheter can also be used via an IABP unit on patients who have a higher level of aortic valve incompetence (which is actually a contraindication for the use of IABP).

In order to operate the pump system as a pump catheter, commercially available IABP balloon catheters can be fitted and operated by sealing the valve. The whole pump catheter is preferably made from biocompatible materials, i.e. there is no reaction with or damage to the organism as a result of the device. Finally, the device may be implanted by a catheter or a guide wire inserted previously, for which an internal lumen is provided.

Although the present invention has been described above by means of preferred embodiments, it is not limited to the above, but may be modified in multiple ways.

LIST OF REFERENCE NUMERALS

1 Device
2 Pump cannula
3 Cannula end with inlet aperture
4 Inlet valve
5 Pump device
6 Inner chamber
7 Outer chamber
8 Outlet valve
9 Drive mechanism
10 Body
11 Left chamber of the heart/left ventricle
12 Outlet valve
13 Outlet valve
14 Right chamber of the heart/right ventricle
15 Outlet aperture
16 Inlet valve
18 A. pulmonalis
19 Right atrium
V. cava superior
V. cava inferior

The invention claimed is:

1. A device for circulating a body fluid in a body of a living organism, to support the heart and/or circulation of the living organism, the device being adapted to support the right chamber of the heart and comprising:
   a catheter device which has at least one inlet portion to take up the body fluid at at least one first location within the body of the living organism, at least one outlet portion some distance from the at least one inlet portion to discharge the body fluid at at least one second location some distance from the at least one first location within the body of the living organism and a pump device for directed transport of the body fluid between the at least one inlet portion and the at least one outlet portion of the catheter device, the pump device comprising a collapsible double chamber cavity with an inner chamber and an outer chamber for inserting and feeding the device solely by means of puncturing the skin via a peripheral vein or artery in the living organism; and a valve arrangement coupled to the catheter device for controlled uptake of the body fluid as a function of operation of the pump device at the at least one inlet portion of the catheter device and controlled discharge of the body fluid at the at least one outlet portion of the catheter device;

wherein the catheter device has a pump cannula and a cannula end at some distance from the pump device, the pump cannula being arranged as a transport pipe between the cannula end and the pump device;

wherein the cannula end forms at least one outlet portion of the catheter device and is formed so as to end in the region of the pulmonary artery;

wherein the at least one inlet portion of the catheter device is located in the region of the pump device, the device being formed in such a manner that the inlet portion can be arranged in the right atrium or the device being formed in such a manner that the inlet portion can be arranged in the vena cava.

2. The device according to claim 1, wherein the valve arrangement has at least one inlet valve which is located in the pump cannula adjacent to the inlet portion.

3. The device according to claim 1, wherein the pump device has a drive mechanism which can be coupled to the inner chamber of the pump device.

4. The device according to claim 3, wherein the drive mechanism is formed as a pneumatic drive mechanism.

5. The device according to claim 1, wherein the valve arrangement has at least one inlet valve in the region of an inlet portion, the at least one inlet valve being arranged on the outer wall of the outer chamber or adjacent portions of the pump device.

6. The device according to claim 1, wherein the valve arrangement has at least one outlet valve, the at least one outlet valve being located on the wall of the pump cannula of the catheter device.

7. The device according to claim 1, wherein the device is made from biocompatible materials for insertion into the body of the living organism without reacting with or damaging the organism.

* * * * *

UNITED STATES PATENT AND TRADEMARK OFFICE
CERTIFICATE OF CORRECTION

PATENT NO. : 8,409,128 B2
APPLICATION NO. : 12/531129
DATED : April 2, 2013
INVENTOR(S) : Markus Ferrari It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 836 days.

Signed and Sealed this
First Day of September, 2015

Michelle K. Lee
*Director of the United States Patent and Trademark Office*